US009138394B2

(12) United States Patent
Giuliani et al.

(10) Patent No.: US 9,138,394 B2
(45) Date of Patent: Sep. 22, 2015

(54) PHARMACEUTICAL, DERMATOLOGICAL, NUTRITIONAL OR COSMETIC COMPOSITION FOR COMBATING THE IMMUNOSUPPRESIVE ACTION OF AGGRESSIVE AGENTS ON THE SKIN

(75) Inventors: Giammaria Giuliani, Milan (IT); Anna Benedusi, Milan (IT)

(73) Assignee: GIULIANI S.P.A., Milan (IT)

( * ) Notice: Subject to any disclaimer, the term of this patent is extended or adjusted under 35 U.S.C. 154(b) by 0 days.

(21) Appl. No.: 13/260,245

(22) PCT Filed: Apr. 30, 2010

(86) PCT No.: PCT/IB2010/051897
§ 371 (c)(1),
(2), (4) Date: Sep. 23, 2011

(87) PCT Pub. No.: WO2010/125541
PCT Pub. Date: Nov. 4, 2010

(65) Prior Publication Data
US 2012/0020902 A1 Jan. 26, 2012

(30) Foreign Application Priority Data
Apr. 30, 2009 (IT) ............................. MI2009A0747

(51) Int. Cl.
*A61K 31/353* (2006.01)
*A61Q 17/04* (2006.01)
*A61K 8/49* (2006.01)
*A61P 37/00* (2006.01)
*A61P 29/00* (2006.01)
*A23L 1/30* (2006.01)
*A61K 9/00* (2006.01)
*A61K 9/06* (2006.01)
*A61K 9/20* (2006.01)
*A61K 9/48* (2006.01)
*A61K 31/352* (2006.01)
*A61Q 19/00* (2006.01)

(52) U.S. Cl.
CPC ............... *A61K 8/498* (2013.01); *A23L 1/3002* (2013.01); *A23L 1/3004* (2013.01); *A61K 9/0014* (2013.01); *A61K 9/0095* (2013.01); *A61K 9/06* (2013.01); *A61K 9/2009* (2013.01); *A61K 9/2054* (2013.01); *A61K 9/4825* (2013.01); *A61K 9/4858* (2013.01); *A61K 31/352* (2013.01); *A61K 31/353* (2013.01); *A61Q 17/04* (2013.01); *A61Q 19/00* (2013.01); *A23V 2002/00* (2013.01); *A61K 2800/92* (2013.01); *A61Q 19/004* (2013.01)

(58) Field of Classification Search
None
See application file for complete search history.

(56) References Cited

U.S. PATENT DOCUMENTS

| 2001/0022978 A1* | 9/2001 | Lacharriere et al. .......... 424/613 |
| 2004/0043047 A1* | 3/2004 | Dumas et al. ................. 424/401 |
| 2008/0069779 A1* | 3/2008 | Tamarkin et al. ............... 424/45 |

FOREIGN PATENT DOCUMENTS

| JP | 2009-075619 | 3/2004 |
| JP | 2009-507826 | 2/2009 |
| WO | WO 01/49285 A1 | 7/2001 |
| WO | WO 02/34262 A1 | 5/2002 |
| WO | WO 02/072035 A2 | 9/2002 |
| WO | WO 2007/029982 | 3/2007 |

OTHER PUBLICATIONS

Huang et al., "Effects of flavonoids on the expression of the pro-inflammatory response in human monocytes induced by ligation of the receptor for AGEs", 2006, Mol. Nutr. Food Res., 50: 1129-1139.*
"Dermatology Focus", 2003, Dermatology Foundation, vol. 22, No. 1, pp. 1-16.*
Katiyar et al., "Green tea and skin cancer: photoimmunology, angiogenesis and DNA repair", 2006, Journal of Nutritional Biochemistry, vol. 18, pp. 287-296.*
Nakagawa et al., "Protective Activity of Green Tea against Free Radical- and Glucose-Mediated Protein Damage", 2002, Journal of Agricultural and Food Chemistry, vol. 50, pp. 2418-2422.*
Santangelo et al., "Polyphenols, intracellular signalling and inflammation", 2007, Ann Ist Super Sanita, vol. 43, No. 4, pp. 394-405.*
Alvarez, P. et al. "Improvement of leukocyte functions in prematurely aging mice after five weeks of diet supplementation with polyphenol-rich cereals," Nutrition, 2006, vol. 22, pp. 913-921.
International Search Report mailed on Jul. 14, 2010 for related International Patent Application No. PCT/IB2010/051897 with Written Opinions, International Filing Date: Apr. 30, 2010, 14 pp.
Lyu S. et al. "Production of Cytokine and NO by RAW 264.7 Macrophanges and PBMC in Vitro Incubation with Flavonoids," Arch Pharm Res, 2005, vol. 28, No. 5, pp. 573-581.
Comalada, M. 2006, "Inhibition of pro-inflammatory markers in primary bone marrow-derived mouse macrophages by naturally occurring flavonoids: Analysis of the structure—activity relationship," *Biochemical Pharmacology*, 72: 1010-1021.
Crouvezier, S., 2001, "The Effects of Phenolic Components of Tea on the Production of Pro- and Anti-Inflammatory Cytokines by Human Leukocytes in Vitro," *Cytokine*, 13(5): pp. 280-286.
Fiala, E.S., 1996, "(--)-Epigalloeatechin gallate, a polyphenolic tea antioxidant, inhibits peroxynitrite-mediated formation of 8-oxodeoxyguanosine and 3-nitrotyrosine," *Experientia*, 52,922-926.

* cited by examiner

*Primary Examiner* — Hasan Ahmed
*Assistant Examiner* — Randeep Singh
(74) *Attorney, Agent, or Firm* — DLA Piper LLP (US)

(57) ABSTRACT

The object of the invention is a mixture of catechin and quercetin in a molar ratio varying between 3:1 and 6:1, respectively, for the treatment of the immunosuppression induced in the skin by aggressive agents such as airborne pollutants, dehydrating agents, ultraviolet radiation, and thermal and osmotic shocks, and a pharmaceutical, dermatological, nutritional or cosmetic composition containing said mixture as an active ingredient.

5 Claims, 2 Drawing Sheets

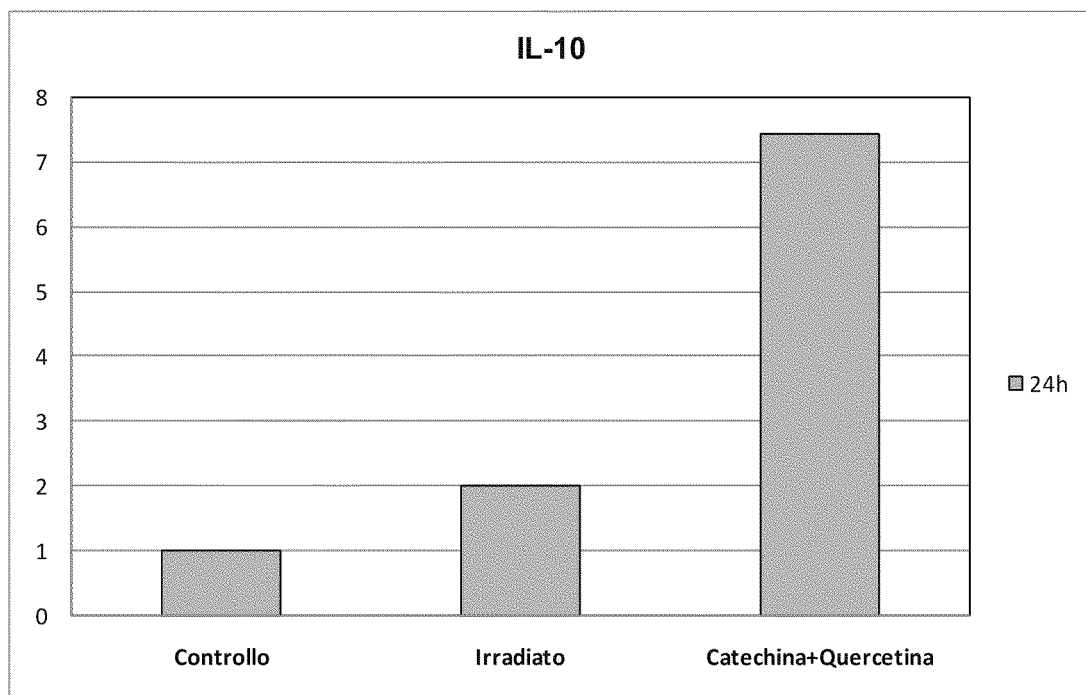
Fig. 1  IL-10 expression (Control – Irradiated – Catechin + Quercetin)
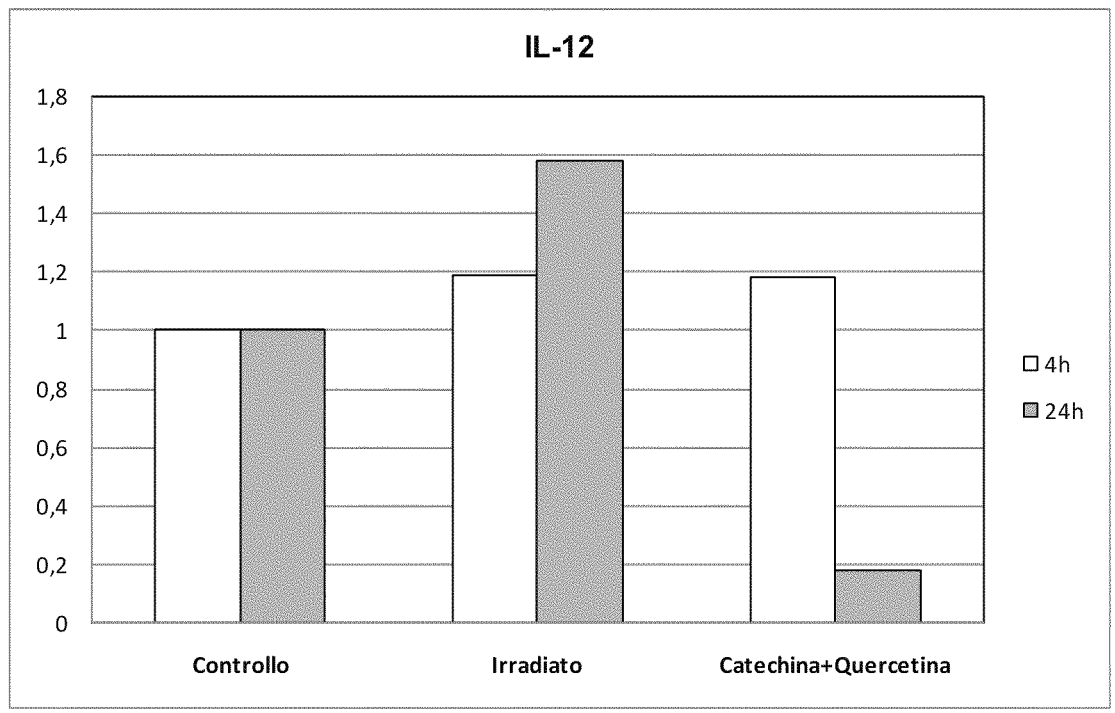
Fig. 2  IL-12 expression (Control – Irradiated – Catechin + Quercetin)

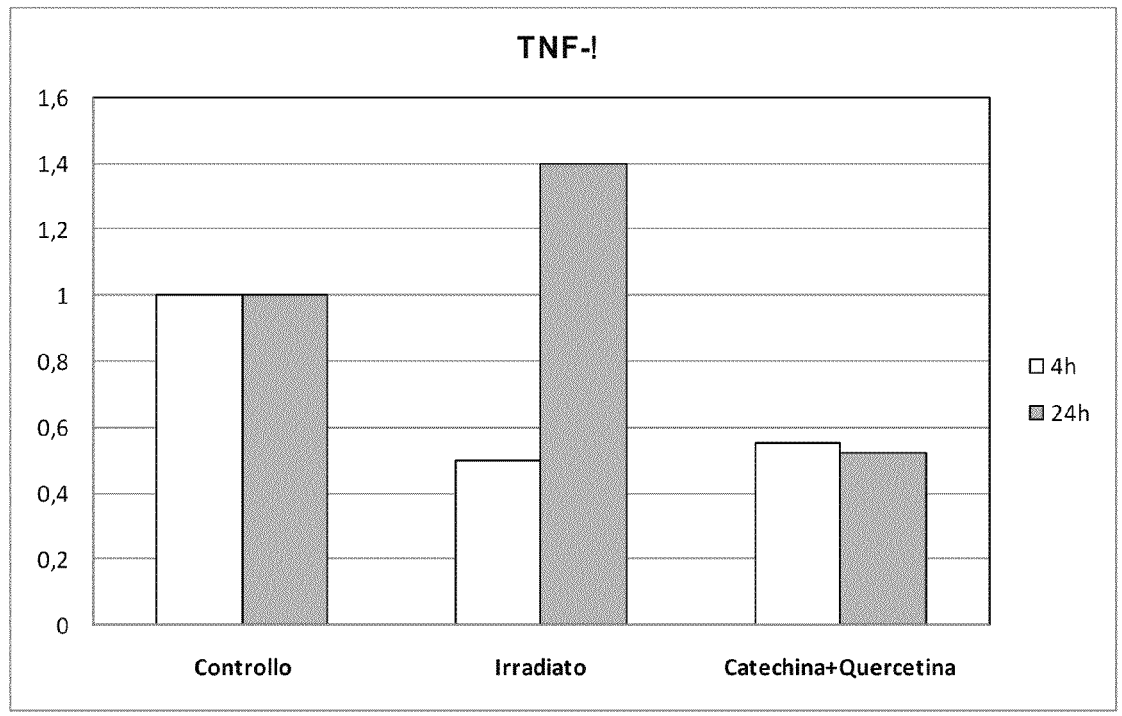
Fig. 3. TNF-α expression (Control – Irradiated – Catechin + Quercetin)
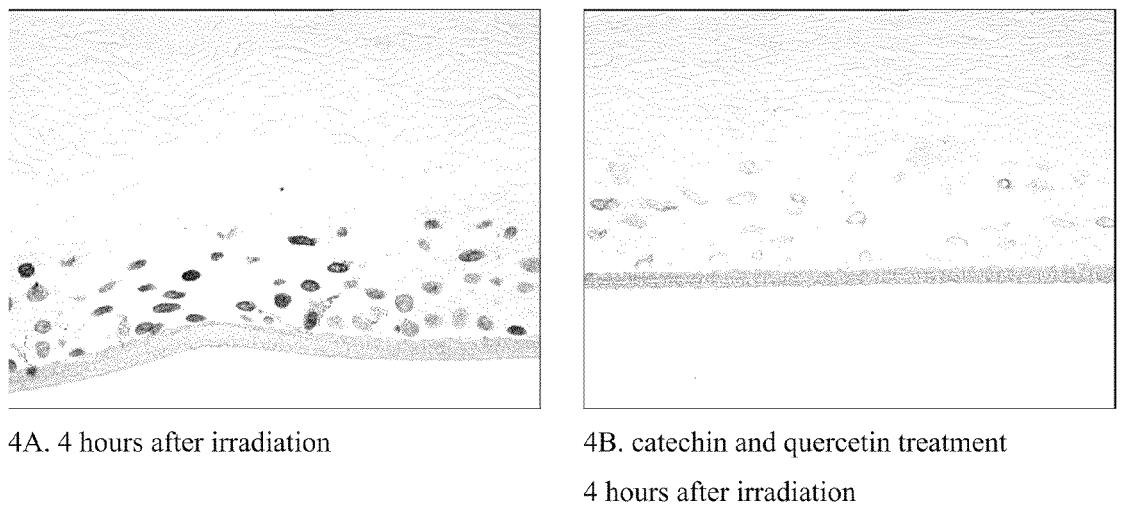
4A. 4 hours after irradiation
4B. catechin and quercetin treatment
4 hours after irradiation
Fig. 4. Immunohistochemistry

PHARMACEUTICAL, DERMATOLOGICAL, NUTRITIONAL OR COSMETIC COMPOSITION FOR COMBATING THE IMMUNOSUPPRESIVE ACTION OF AGGRESSIVE AGENTS ON THE SKIN

CROSS REFERENCE TO RELATED APPLICATIONS

This application is a national phase entry of International Application No. PCT/IB2010/051897 filed on Apr. 30, 2010, which in turn claims priority to Italian Patent priority No. MI2009A000747 filed on Apr. 30, 2009; each of which is hereby incorporated by reference herein in its entirety.

FIELD OF THE INVENTION

The skin provides an effective barrier against the harmful effects of the environment, protecting the body's internal organs. The main layers of the skin include the epidermis, the dermis and the hypodermis. The human epidermis is quite thick and comprises up to 15 layers. It represents the body's first defensive barrier against physical, chemical and environmental harmful agents, including ultraviolet radiation, for instance, thermal and osmotic shocks, and the airborne pollutants that are increasingly widespread in the environment nowadays.

Suppression of the skin's immune system is known to be one of the mechanisms by means of which such harmful agents can induce, for instance, the onset of skin tumours, mainly affecting the epidermal layer and the corresponding cells.

To give an example, ultraviolet radiation induces both immediate and late changes in the skin during and after the period of exposure. In addition to visible changes, such as the formation of sunstroke-induced cells (known as "sunburn cells"), the production of melanin by the melanocytes and a thickening of the corneal layer due to the action of specific cytokeratins, several changes occurring at molecular level are responsible for potential long-term damage, such as: endogenous antioxidant depletion, which occurs in the hours immediately after exposure to radiation and induces a cascade of late degenerative reactions (known as oxidative stress) affecting the skin's whole structure, epidermis and dermis; the immune reaction in which the protagonists are the Langerhans cells, the reaction being mediated by cytokines and other soluble factors; molecular damage to the DNA, particularly through the formation of 8-oxy D guanosine.

STATE OF THE ART

As references in the literature on this topic, concerning the immunosuppressive effects of ultraviolet radiation, it is worth mentioning the following:

Katiyar S, Elmets C A, Katiyar S K. Green tea and skin cancer: photoimmunology, angiogenesis and DNA repair. J Nutr Biochem. 2007 May; 18(5):287-96.

Skiba B, Neill B, Piva T J. Gene expression profiles of TNF-alpha, TACE, furin, IL-1beta and matrilysin in UVA- and UVB-irradiated HaCat cells. Photodermatol Photoimmunol Photomed. 2005 August; 21(4):173-82.

Yawalkar N, Limat A, Brand C U, Braathen L R. Constitutive expression of both subunits of interleukin-12 in human keratinocytes. J Invest Dermatol. 106(1):80-3, 1996.

Curiel-Lewandrowski C, Venna S S, Eller M S, Cruikshank W, Dougherty I, Cruz P D Jr, Gilchrest B A. Inhibition of the elicitation phase of contact hypersensitivity by thymidine dinucleotides is in part mediated by increased expression of interleukin-10 in human keratinocytes. Exp Dermatol. 2003 April; 12(2):145-52.

Schwarz T. Mechanisms of UV-induced immunosuppression. Keio J. Med. 2005 December; 54(4):165-71.

The object of the present invention is to provide a means for effectively combating the immunosuppressive action on the skin of aggressive agents, e.g. airborne pollutants, dehydrating agents, ultraviolet radiation, thermal and osmotic shocks, and others.

EP1328268, owned by the same applicant, describes the antioxidant activity of a combination of the flavonoids catechin and quercetin, based particularly on a clinical study that demonstrated a marked platelet aggregation inhibitory activity. Said patent also suggested an antioxidant activity that contrasted the skin ageing effect of ultraviolet radiation.

Generally speaking, however, it is impossible to say whether the antioxidant activity of a given compound, or combination of compounds, can coincide with an action against immunosuppressive effects and consequently with an immunoprotective activity of the type discussed above.

SUMMARY OF THE INVENTION

According to the present invention, it has surprisingly been discovered from the outcome of an experimental study that catechin and quercetin, combined together in a selected quantitative ratio, constitute an effective active ingredient for combating the immunosuppressive action on the skin of the above-mentioned aggressive agents.

DETAILED DESCRIPTION OF THE INVENTION

Below are the structural formulas and molecular weights of catechin and quercetin:

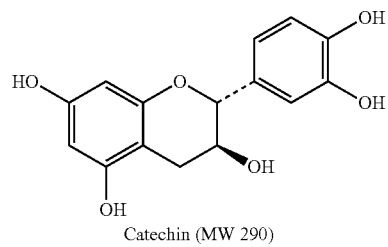
Catechin (MW 290)

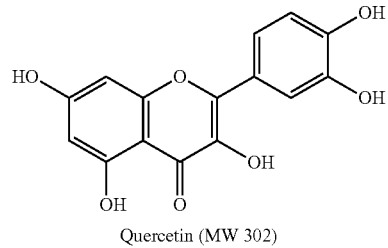
Quercetin (MW 302)

The object of the present invention is thus the use of said combination as an active ingredient in the preparation of a pharmaceutical, dermatological, nutritional or cosmetic composition for combating the immunosuppressive action on the skin of aggressive agents such as airborne pollutants, dehydrating agents, ultraviolet radiation, thermal and osmotic shocks, and the corresponding composition, characterised in that it comprises as active ingredient a combination of catechin and quercetin in a molar ratio approximately in the range of 6:1 and 3:1, respectively.

The composition according to the invention can be formulated for topical use on the skin or for systemic use, e.g. in a form suitable for oral administration.

Below are several descriptions of compositions according to the present invention, which shall not be intended as limiting.

In examples 1-5, the quantities of the components are expressed as weight to weight percentages within a given range, as stated below. For quercetin, on the other hand, a molar ratio of quercetin to catechin of 1:5 is indicated, in relation to the quantity of catechin chosen within said stated range.

Example 1

Sun Milk

| Component (INCI name) | Quantity % w/w |
|---|---|
| PEG-30 dipolyhydroxystearate | 2.00-5.00 |
| Polyglyceryl-4 diisostearate polyhydroxystearate Sebacate | 2.00-6.00 |
| Batyl alcohol | 0.03-0.080 |
| Ethylhexyl methoxycinnamate | 5.00-11.00 |
| Diethylamino hydroxybenzoylhexyl benzoate | 5.00-11.00 |
| Butyl methoxydibenzoylmethane | 1.00-4.00 |
| Ethylhexyl salicylate | 1.00-5.000 |
| Caprylic/capric triglyceride | 1.00-10.00 |
| C12-15 alkyl benzoate | 3.00-10.00 |
| Butylene glycol dicaprylate/dicaprate | 4.00-10.00 |
| Diisopropyl sebacate | 1.00-5.00 |
| *Butyrospermum parkii* butter | 0.40-3.00 |
| *Zea mays* oil | 0.50-1.00 |
| *Persea gratissima* oil unsaponifiables | 0.40-2.00 |
| *Calendula officinalis* | 1.00-5.00 |
| Triethyl citrate | 0.20-0.80 |
| Vp/eicosene copolymer | 0.30-2.00 |
| Glyceryl behenate/eicosadioate | 1.00-3.00 |
| Pentaerythrityl tetra-di-t-butyl Hydroxyhydrocinnamate | 0.01-0.050 |
| Ethylhexyl triazone | 1.00-4.00 |
| Magnesium stearate | 0.10-0.80 |
| Beta-sitosterol | 0.05-0.50 |
| Benzoic acid | 0.20-0.50 |
| Triclosan | 0.02-0.70 |
| Glycyrrhetinic acid | 0.02-0.70 |
| Boron nitride | 0.20-0.50 |
| Titanium dioxide | 0.50-5.00 |
| Aluminum hydroxide | 0.50-5.00 |
| Stearic acid | 0.50-3.00 |
| Glycerin | 1.00-5.00 |
| Sorbityl furfural | 0.10-0.90 |
| Catechin | 0.005-0.05 |
| Magnesium sulphate | 0.70 |
| Cyclopentasiloxane | 1.00-5.00 |
| Caprylyl glycol | 0.10-0.80 |
| Quercetin | 1:5 (molar ratio of quercetin to catechin) |
| Tetrasodium dicarboxymethyl glutamate | 0.10-0.05 |
| Parfum | 0.20 |
| Bis-ethylhexyl hydroxydimethoxy benzylmalonate | 0.01-0.50 |
| Hydrogenated lecithin | 0.05-1.00 |
| Aqua | q.s. 100 g |

Example 2

Sun Milk

| Component (INCI name) | Quantity w/w (%) |
|---|---|
| C10-18 triglycerides | 1.00-10.00 |
| C12-15 alkyl benzoate | 3.00-10.00 |
| Butylene glycol dicaprylate/dicaprate | 4.00-10.00 |
| Diisopropyl sebacate | 1.00-5.00 |
| Behenyl alcohol | 0.40-3.00 |
| Squalane | 0.40-2.00 |
| PEG-30 dipolyhydroxystearate | 2.00-5.00 |
| Polyglyceryl-4 diisostearate/ Polyhydroxystearate/sebacate | 2.00-6.00 |
| Batyl alcohol | 0.03-0.08 |
| Ethylhexyl methoxycinnamate | 5.00-11.00 |
| Diethylamino hydroxybenzoyl hexyl benzoate | 5.00-11.00 |
| Butyl methoxydibenzoylmethane | 1.00-4.00 |
| Ethylhexyl salicylate | 1.00-5.00 |
| *Zea mays* oil | 0.50-1.00 |
| *Calendula officinalis* | 1.00-5.00 |
| Triethyl citrate | 0.20-0.80 |
| Vp/eicosene copolymer | 0.30-2.00 |
| Glyceryl behenate/eicosadioate | 1.00-3.00 |
| Pentaerythrityl tetra-di-t-butyl hydroxyhydrocinnamate | 0.01-0.050 |
| Ethylhexyl triazone | 1.00-4.000 |
| Magnesium stearate | 0.10-0.80 |
| Beta-sitosterol | 0.05-0.50 |
| Benzoic acid | 0.20-0.50 |
| Triclosan | 0.02-0.70 |
| Glycyrrhetinic acid | 0.02-0.70 |
| Boron nitride | 0.20-0.50 |
| Titanium dioxide | 0.50-5.00 |
| Aluminum hydroxide | 0.50-5.00 |
| Stearic acid | 0.50-3.00 |
| Glycerin | 1.00-5.00 |
| Catechin | 0.005-0.05 |
| Magnesium sulphate | 0.10-0.80 |
| Cyclopentasiloxane | 1.00-5.00 |
| Caprylyl glycol | 0.50-0.800 |
| Sorbityl furfural | 0.10-0.90 |
| Quercetin | 1:5 (molar ratio of quercetin to catechin) |
| Tetrasodium dicarboxymethyl glutamate | 0.10-0.05 |
| Parfum | 0.200 |
| *Coleus forskohlii* root extract | 0.01-0.10 |
| Bis-ethylhexyl hydroxydimethoxy Benzylmalonate | 0.01-0.50 |
| Hydrogenated lecithin | 0.05-1.00 |
| Aqua | q.s. 100 g |

Example 3

Sun Cream

| Component (INCI name) | Quantity w/w (%) |
|---|---|
| PEG-30 dipolyhydroxystearate | 1.00-5.00 |
| Polyglyceryl-4 diisostearate polyhydroxystearate sebacate | 1.00-5.00 |
| Batyl alcohol | 0.03-0.08 |
| Ethylhexyl methoxycinnamate | 5.00-11.00 |
| Butyl methoxydibenzoylmethane | 0.50-1.00 |
| Diethylamino hydroxybenzoyl hexyl benzoate | 5.00-11.00 |
| Ethylhexyl salicylate | 2.00-7.00 |
| Caprylic/capric triglyceride | 3.00-8.00 |
| C12-15 alkyl benzoate | 3.00-8.00 |
| Butylene glycol dicaprylate/dicaprate | 3.00-8.00 |
| Diisopropyl sebacate | 1.00-6.00 |
| *Butyrospermum parkii* butter | 0.40-3.00 |
| *Persea gratissima* oil unsaponifiables | 0.40-3.00 |

-continued

| Component (INCI name) | Quantity w/w (%) |
|---|---|
| Olea europea | 0.40-3.00 |
| Calendula officinalis extract | 0.40-3.00 |
| Vp/eicosene copolymer | 0.50-1.20 |
| Glyceryl behenate/eicosadioate | 2.00-3.50 |
| Triethyl citrate | 0.10-0.60 |
| Pentaerythrityl tetra-di-t-butyl hydroxyhydrocinnamate | 0.025-0.050 |
| Ethylhexyl triazone | 1.00-2.500 |
| Beta-sitosterol | 0.05-0.300 |
| Benzoic acid | 0.20-0.30 |
| Triclosan | 0.20-0.500 |
| Glycyrrhetinic acid | 0.020-0.500 |
| Boron nitride | 0.020-0.500 |
| Sorbityl furfural | 0.10-0.90 |
| Glycerin | 1.00-5.00 |
| Magnesium sulphate | 0.02-0.90 |
| Xanthan gum | 0.20-0.40 |
| Cyclopentasiloxane | 1.00-3.50 |
| Catechin | 0.005-0.05 |
| Quercetin | 1:5 (molar ratio of quercetin to catechin) |
| Caprylyl glycol | 0.50-0.800 |
| Silica dimethyl silylate | 1.00-3.00 |
| Aluminum starch octenylsuccinate | 1.00-3.00 |
| Tetrasodium dicarboxymethyl glutamate | 0.10-0.50 |
| Coleus forskohlii root extract | 0.005-0.05 |
| Bis-ethylhexyl hydroxydimethoxy benzylmalonate | 0.10-0.50 |
| Hydrogenated lecithin | 0.05-0.150 |
| Parfum | 0.20 |
| Aqua | q.s. 100 g |

Example 4

Aftersun Body Milk

| Component (INCI name) | Quantity w/w (%) |
|---|---|
| Glycerin | 1.00-6.00 |
| Cetyl hydroxyethylcellulose | 0.10-0.40 |
| Xanthan gum | 0.10-0.40 |
| Allantoin | 0.10-0.35 |
| Tapioca starch | 1.00-4.00 |
| Sodium hyaluronate | 0.025-0.35 |
| Disodium EDTA | 0.025-0.20 |
| Catechin | 0.005-0.05 |
| Quercetin | 1:5 (molar ratio of quercetin to catechin) |
| Sorbitan stearate | 2.00-5.00 |
| Sucrose cocoate | 0.10-1.00 |
| Glycyrrhetinic acid | 0.30-0.70 |
| Squalane | 2.00-5.00 |
| Beta-sitosterol | 0.10-0.50 |
| Caprylic/capric triglycerides | 1.00-5.00 |
| Butyrospermum parkii | 1.00-5.00 |
| Calendula officinalis | 1.00-3.00 |
| Dimethicone | 1.00-3.00 |
| Sodium hydroxymethylglycinate | 0.25-0.50 |
| Parfum | 0.30 |
| Delta tocopherol | 0.02-0.25 |
| Sorbityl furfural | 0.10-0.90 |
| Aqua | q.s. 100 g |
| Lactic acid (pH corrector) | q.s. |

Example 5

Aftersun Face Cream

| Component (INCI name) | Quantity w/w (%) |
|---|---|
| Glycerin | 2.0-5.0 |
| Tapioca starch | 1.00-2.00 |
| Cetyl hydroxyethylcellulose | 0.10-0.50 |
| Sodium hyaluronate | 0.05-0.5 |
| Tetrasodium EDTA | 0.10-0.50 |
| Catechin | 0.005-0.05 |
| Quercetin | 1:5 (molar ratio of quercetin to catechin) |
| Glycyrrhetinic acid | 0.10-0.70 |
| Cetearyl olivate | 1.00-4.00 |
| Sorbitan olivate | 0.50-3.00 |
| Butyrospermum parkii | 1.0-8.00 |
| Cetostearyl alcohol | 0.50-2.00 |
| Beta sitosterol | 0.10-0.50 |
| Delta tocopherol | 0.05-0.20 |
| Dimethicone | 0.50-1.50 |
| Dimethicone crosspolymer | 0.20-1.50 |
| Sorbityl furfural | 0.5-1.00 |
| Calendula officinalis | 0.50-5.00 |
| Sodium hydroxymethylglycinate | 0.25-0.50 |
| Parfum | q.s. |
| Aqua | q.s. 100.00 |

Example 6

Dietary Product for Preventing Damage Due to Induced Skin Immunosuppression

| Each soft gelatin capsule (pearl) contains: | |
|---|---|
| Catechin | 80 mg |
| Quercetin | 20 mg |
| Vitamin E (dl-alpha tocopherol) | 5 mg |
| Soy oil | 290 mg |
| Soy lecithin | 5 mg |
| Mono- and diglycerides of fatty acids | 30 mg |
| Capsule ingredients: | |
| Gelatin | 145 mg |
| Glycerol | 67 mg |

Example 7

Dietary Product in Tablet Form for Preventing Damage Due to Induced Skin Immunosuppression

| Each tablet contains L-arginine hydrochloride | 200-250 mg |
|---|---|
| Microcrystalline cellulose | 100-250 mg |
| Dibasic calcium phosphate dihydrate | 100-200 mg |
| Hydroxypropylmethylcellulose | 30-100 mg |
| Zinc (as amino acid chelate) | 7.5 mg |
| Copper (as amino acid chelate) | 1.2 mg |
| Catechin | 4.03 mg |
| Quercetin | 0.84 mg |
| Mono- and diglycerides of fatty acids (E471) | 5-10 mg |
| Silicon dioxide (colloidal silica) | 5-10 mg |

Example 8

Dietary Product in Firm Gelatin Capsules for Preventing Damage Due to Induced Skin Immunosuppression Each Firm Gelatin Capsule Contains:

| | |
|---|---|
| Quercetin | 10.4 mg |
| Catechin | 40 mg |
| Lysine monohydrochloride | 110 mg |
| Dibasic calcium phosphate dihydrate | 50-100 mg |
| Microcrystalline cellulose | 50-100 mg |
| Magnesium stearate | 5-10 mg |
| Silicon dioxide | 3-6 mg |
| Natural gelatin | capsule |

-continued

| | |
|---|---|
| Red iron oxide (Coloring agent E172) | 0.44 mg |
| Biotin | 0.17 mg |

Example 9

Dietary Product for Preventing Damage Due to Induced Skin Immunosuppression—Soft Gelatin Capsule (Pearl)

| Each soft gelatin capsule (pearl) contains: | |
|---|---|
| Quercetin | 17 mg |
| Catechin | 83 mg |
| Vitamin E (dl-alpha tocopherol) | 5 mg |
| Borage oil | 50 mg |
| Soy oil | 350 mg |
| Soy lecithin | 5 mg |
| Mono- and di-glycerides of fatty acids | 30 mg |
| Capsule ingredients: | |
| Gelatin | 145 mg |
| Glycerol | 67 mg |

Example 10

Dietary Product in Tablet Form for Preventing Damage Due to Induced Skin Immunosuppression Each Tablet Contains:

| | |
|---|---|
| d-Biotin | 0.23 mg |
| Ubidecarenone | 10 mg |
| Vitamin C | 60 mg |
| Vitamin E (dl-alpha tocopherol) | 15 mg |
| *Vitis vinifera* dry extract of seeds and leaves | 60 mg |
| (containing catechin and quercetin in a molar ratio of 5:1) | |
| Pyridoxine hydrochloride | 3.6 mg |
| Luteine | 2 mg |
| Zinc (as amino acid chelate) | 7.5 mg |
| Copper (as amino acid chelate) | 1.2 mg |
| Manganese (as amino acid chelate) | 1.75 mg |
| Hydroxypropylmethylcellulose | 30-50 mg |
| Dibasic calcium phosphate dihydrate | 50-100 mg |
| Microcrystalline cellulose | 50-100 mg |
| Magnesium stearate | 5-10 mg |
| Silicon dioxide | 3-6 mg |

Example 11

Dietary Product for Preventing Damage Due to Induced Skin Immunosuppression—Single-Dose Sachets Each Sachet Contains:

| | |
|---|---|
| *Vitis vinifera* dry extract of seeds and leaves | 60 mg |
| (containing catechin and quercetin in a molar ratio of 5:1) | |
| Liophylised *Lactobacillus plantarum* | 1'000'000 UFC/dose |
| Leucine | 10-20 mg |
| Maltodextrin | 500-1000 mg |

The efficacy of the active ingredient according to the invention was tested by means of in vitro experiments.

BRIEF DESCRIPTION OF THE FIGURES

The experimental study is described below with reference to the graphs in the attached figures.

FIG. 1 shows a graph referring to the expression of the cytokine IL-10.

FIG. 2 shows a graph referring to the expression of the cytokine IL-12.

FIG. 3 shows a graph referring to the expression of TNF-α according to the detailed description given below.

FIG. 4 shows the immunohistochemistry of the thymine dimers in the irradiated sample (1 MED), with and without treatment with the catechin and quercetin combination 4 hours after irradiation.

IN VITRO STUDY

Introduction and Aim

This study was conducted on human epidermis reconstructed in vitro to assess the immunoprotective and preventive action of the combination of catechin and quercetin against DNA damage induced by UVA and UVB radiation at a minimum erythematous dose (1 MED).

UV-induced DNA damage is known to be one of the main molecular mediators of photo-immunosuppression (Schwarz et al., 2005).

A study conducted by the Kripke group (1992) clearly demonstrated that the DNA is the preferential target of UV radiation in the process of eliciting systemic immunosuppression, and that the primary molecular event mediating this type of UV-induced immunosuppression is the formation of pyrimidine dimers. In particular, the methods specifically active against this type of DNA lesion are effective tools for restoring immunological function.

In parallel with the study on UV-induced DNA damage, the pro-inflammatory cytokines TNF-alpha and IL-12, and the anti-inflammatory cytokine IL-10 were also analysed.

The experimental approach adopted for the study as a whole enabled us to identify already in an early stage (and consequently very important for its dermatological action in preventing photo-induced damage) the degree of activity of the molecules considered in combating the immunosuppression processes induced by UV radiation in a physiological condition of vital epidermis submitted to UV-induced stress; this was done using relevant, dynamic and highly sensitive parameters, such as the expression of mediators and damage to the DNA at molecular level.

It is well known that certain cytokines, and the interleukin IL-12 in particular, have an immunomodulating activity in relation to the immunocompetent cells, i.e. the Langerhans cells. We consequently decided to use this early mechanism of epidermal keratinocyte-mediated immune response following UV radiation to evaluate the activity of the compounds considered here.

IL-10 is a crucial factor for preserving the fine balance between resistance to pathogens and harmful systemic inflammation, and it is a powerful inhibitor of IL-12 production (Haste-Amezaga et al., 1998, D'Andrea et al., 1993).

IL-12 expression in the epidermal keratin cells after UV radiation was assessed using the RT-PCR method.

The protective effect against DNA damage was judged from the formation of dimers with a pyrimidine base (thymine) at basal and supra-basal epidermal level, which becomes apparent already 4 hours after exposure: these dimers are recognized markers of NMSC (non-melanoma skin cancer) and their formation is assessed by immunohistochemistry. The immunohistochemical examination of the tissues treated with catechin and quercetin showed a more limited immunostaining, indicative of a reduction of the thymine dimers. FIG. 4 shows images of the immunohistochemical slides of the thymine dimers, with the untreated irradiated sample (1 MED) on the left and the sample treated with the catechin and quercetin mixture according to the invention on the right, 4 hours after irradiation, showing the more limited cell staining in the latter.

The same method was used to assess the formation of 8-oxy D-guanosine, a specific marker of UVA-induced DNA damage.

For this experiment, we used 0.9% physiological solution as the inactive control substance and a mixture containing catechin and quercetin, in a weight/weight ratio of 5:1, dissolved in physiological solution as the composition according to the invention.

FIGS. 1-3 in the attached drawings show graphs relating to the expressions of IL-10, IL-12 and TNF-alpha obtained for an unirradiated control, an untreated irradiated control and an irradiated sample treated with the composition according to the invention (catechin+quercetin).

Each pair of adjacent columns in the graphs refers to the case of a 4-hour UV treatment (paler column on the left, 4 h) and a 24-hour treatment (darker column on the right, 24 h), respectively, irradiated as in 1MED.

Results

The outcome of a histological assessment using immunofluorescence demonstrated that:
a) 8 oxy D-guanosine, a biomarker of UVA-induced oxidative stress: 4 hours after irradiation, the catechin and quercetin mixture demonstrated a protective effect, since the formation of 8 oxy was inhibited by comparison with the irradiated control;
b) thymine dimers: there was evidence of the inhibition of pyrimidine dimer formation 4 hours after exposure in the mixture treated with catechin and quercetin.

The increased IL-10 levels by comparison with the unirradiated control, after UV radiation with and without catechin+quercetin treatment, are evidence of the immunosuppression-oriented changes occurring in the cutaneous environment (FIG. 1).

On the other hand, the predominance of IL-10 over IL-12 (FIG. 2) is essential to favouring the regression of the inflammatory response after UV radiation. In particular, a picture of higher IL-10 levels and lower IL-12 levels in the skin is consistent with the immunosuppressive effect of UV exposure and the skin's need to restrict the inflammatory response (Kang et al., 1997).

IL-12 is also suppressed by TNF-alpha, another cytokine closely linked to IL-12 in regulating inflammatory response and IFN-gamma production (Ma and Trinchieri, 2001). TNF-alpha has a key role as a mediator of UV-induced skin damage (Barr et al., 1999).

UV exposure prompts an increment in TNF-alpha levels, while treatment with catechin and quercetin leads to a reduction of TNF-alpha levels.

This finding, as illustrated in FIG. 3, is closely related to the increase that catechin+quercetin treatment induces in IL-10 levels, since IL-10 is a powerful inhibitor of TNF-alpha (Bogdan et al., 1991).

Conclusions

The results of the above-described study globally demonstrated a surprisingly protective action of the catechin and quercetin mixture according to the invention, associated with an anti-inflammatory activity emerging from the evidence of the protective action against DNA damage induced by UVA and/or UVB, and of the IL-10 and TNF-alpha expression levels.

The effective achievement of the objects of the invention was thus demonstrated.

The invention claimed is:

1. A method of treatment of the human skin by protective action thereof from immunosuppression induced in the skin by aggressive agents including airborne pollutants, dehydrating agents, ultraviolet rays, and thermal and osmotic shocks, wherein the method comprises:
administering topically an effective amount of a mixture of catechin and quercetin in a molar ratio approximately in the range of 6:1 to 3:1, as an active ingredient in a pharmaceutical, dermatological, nutritional or cosmetic composition, to effect the protective action against immunosuppression in the skin, wherein the protective action comprises a combination of increased IL-10 expression, reduced IL-12 or TNF-α expression, inhibition of thymine dimers, and inhibition of 8 oxy D-guanosine, and wherein the protective action on the skin comprises an anti-inflammatory activity.

2. The method of claim 1, wherein the catechin and quercetin mixture is in a molar ratio of approximately 5:1, respectively.

3. The method of claim 1, wherein the catechin and quercetin mixture is formulated in a composition for topical use.

4. A pharmaceutical, dermatological, nutritional or cosmetic composition to effect a protective action against immunosuppression induced in the skin by aggressive agents including airborne pollutants, dehydrating agents, and thermal and osmotic shocks, characterized in that it comprises as active ingredient an effective amount of a mixture of catechin and quercetin in a molar ratio approximately in the range of 6:1 to 3:1, respectively, to effect the protective action, wherein the protective action comprises a combination of increased IL-10 expression, reduced IL-12 or TNF-α expression, inhibition of thymine dimers, and inhibition of 8 oxy D-guanosine, and an anti-inflammatory activity, wherein the composition is formulated for topical use.

5. The composition as claimed in claim 4, characterized in that said active ingredient consists of a catechin and quercetin mixture in a molar ratio of approximately 5:1.

* * * * *